United States Patent
Gliner et al.

(10) Patent No.: US 11,000,220 B2
(45) Date of Patent: May 11, 2021

(54) SNR OF INTRACARDIAC SIGNALS

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 506 days.

(21) Appl. No.: 15/919,863

(22) Filed: Mar. 13, 2018

(65) Prior Publication Data

US 2019/0282117 A1  Sep. 19, 2019

(51) Int. Cl.
| A61B 5/05 | (2021.01) |
| A61B 5/06 | (2006.01) |
| A61B 5/333 | (2021.01) |
| A61B 5/00 | (2006.01) |
| A61B 5/287 | (2021.01) |

(52) U.S. Cl.
CPC .............. *A61B 5/333* (2021.01); *A61B 5/287* (2021.01); *A61B 5/6885* (2013.01); *A61B 5/7203* (2013.01); *A61B 5/7221* (2013.01)

(58) Field of Classification Search
CPC .. A61B 5/00; A61B 5/04; A61B 5/042; A61B 5/06; A61B 5/743; A61B 5/6886; A61B 5/6858; A61B 5/04012; A61B 5/063
See application file for complete search history.

(56) References Cited

U.S. PATENT DOCUMENTS

| 4,537,200 | A | 8/1985 | Widrow |
| 6,915,149 | B2 | 7/2005 | Ben-Haim |
| 8,456,152 | B2 | 6/2013 | Garland et al. |
| 10,398,348 | B2* | 9/2019 | Osadchy ................ A61B 5/743 |
| 2001/0039385 | A1 | 11/2001 | Ellenz |
| 2007/0179390 | A1 | 8/2007 | Schecter |
| 2010/0041975 | A1 | 2/2010 | Chen |
| 2012/0089040 | A1 | 4/2012 | Stahmann et al. |
| 2012/0157804 | A1 | 6/2012 | Rogers et al. |
| 2014/0088394 | A1 | 3/2014 | Sunderland |
| 2014/0257119 | A1 | 9/2014 | LeMay |
| 2017/0135640 | A1 | 5/2017 | Gunasekar |

FOREIGN PATENT DOCUMENTS

EP  3254613 A2  12/2017

OTHER PUBLICATIONS

U.S. Appl. No. 15/610,865, filed Jun. 1, 2017.
U.S. Appl. No. 15/788,286, filed Oct. 19, 2017.
European Search Report for corresponding EPA No. 19162243.0 dated Aug. 1, 2019.

* cited by examiner

*Primary Examiner* — Jon Eric C Morales

(57) ABSTRACT

Described embodiments include a system, including sample-and-hold circuitry, configured to sample a plurality of intracardiac electrocardiographic (ECG) signals acquired by respective electrodes disposed within a heart of a subject, and a processor. The processor is configured to receive, from one or more contact-indicating sensors, contact-indicating signals that indicate respective likelihoods of the electrodes being in contact with tissue of the heart, and, in response to the likelihoods being different from each other, cause the ECG signals to be sampled, by the sample-and-hold circuitry, at different respective sampling frequencies. Other embodiments are also described.

17 Claims, 2 Drawing Sheets

SNR OF INTRACARDIAC SIGNALS

FIELD OF THE INVENTION

The present invention relates to the acquisition of physiological data from a subject.

BACKGROUND

In some cases, a catheter device comprising one or more electrodes is used to acquire intracardiac electrocardiographic (ECG) signals from a subject.

SUMMARY OF THE INVENTION

There is provided, in accordance with some embodiments of the present invention, a system that includes sample-and-hold circuitry, configured to sample a plurality of intracardiac electrocardiographic (ECG) signals acquired by respective electrodes disposed within a heart of a subject, and a processor. The processor is configured to receive, from one or more contact-indicating sensors, contact-indicating signals that indicate respective likelihoods of the electrodes being in contact with tissue of the heart, and, in response to the likelihoods being different from each other, cause the ECG signals to be sampled, by the sample-and-hold circuitry, at different respective sampling frequencies.

In some embodiments, the system further includes a multiplexer, configured to:
receive the ECG signals from the electrodes, and
pass the received ECG signals, over a set of channels, to the sample-and-hold circuitry,
the sample-and-hold circuitry being configured to sample the ECG signals by sampling the channels.

In some embodiments, the processor is configured to cause the ECG signals to be sampled at the different respective sampling frequencies by causing the multiplexer to pass the ECG signals to the sample-and-hold circuitry over different respective numbers of the channels.

In some embodiments, the processor is configured to cause the ECG signals to be sampled at the different respective sampling frequencies by varying the respective numbers of the channels over multiple sampling cycles of the sample-and-hold circuitry.

In some embodiments, the multiplexer is configured to pass the ECG signals to the sample-and-hold circuitry over respective ones of the channels, and the processor is configured to cause the ECG signals to be sampled at the different respective sampling frequencies by causing the sample-and-hold circuitry to sample the respective ones of the channels at the different respective sampling frequencies.

In some embodiments,
the electrodes include a first electrode and a second electrode,
the ECG signals include a first ECG signal from the first electrode, and a second ECG signal from the second electrode,
the likelihoods include a first likelihood of the first electrode being in contact with the tissue, and a second likelihood of the second electrode being in contact with the tissue, and
the processor is configured to cause the first ECG signal to be sampled at a greater frequency than the second ECG signal, in response to the first likelihood being greater than the second likelihood.

In some embodiments, the processor is configured to cause the second ECG signal to not be sampled during at least one sampling cycle of the sample-and-hold circuitry, in response to the first likelihood being greater than the second likelihood.

There is further provided, in accordance with some embodiments of the present invention, a method that includes receiving, from one or more contact-indicating sensors, contact-indicating signals that indicate respective likelihoods of a plurality of electrodes being in contact with tissue of a heart of a subject, while the electrodes acquire respective intracardiac electrocardiographic (ECG) signals from the tissue. The method further includes, in response to the likelihoods being different from each other, causing the ECG signals to be sampled, by sample-and-hold circuitry, at different respective sampling frequencies.

There is further provided, in accordance with some embodiments of the present invention, a computer software product including a tangible non-transitory computer-readable medium in which program instructions are stored. The instructions, when read by a processor, cause the processor to receive, from one or more contact-indicating sensors, contact-indicating signals that indicate respective likelihoods of a plurality of electrodes being in contact with tissue of a heart of a subject, while the electrodes acquire respective intracardiac electrocardiographic (ECG) signals from the tissue. The instructions further cause the processor to cause the ECG signals to be sampled, by sample-and-hold circuitry, at different respective sampling frequencies, in response to the likelihoods being different from each other.

The present invention will be more fully understood from the following detailed description of embodiments thereof, taken together with the drawings, in which:

DETAILED DESCRIPTION OF EMBODIMENTS

Overview

In embodiments of the present invention, a plurality of electrodes acquire respective intracardiac ECG signals (or "electrograms") from the heart of a subject. The signals are received by an integrated circuit (IC), such as an application-specific integrated circuit (ASIC), over a set of channels. The IC comprises sample-and-hold circuitry (which, for convenience, is referred to herein as a "sampler") and quantizing circuitry (referred to herein as a "quantizer"), which digitize the received signals.

Hypothetically, each of the signals could be passed through a different respective one of the channels, and the sampler could continually cycle through the channels, such as to attain the same sample rate (or "sampling frequency") for all of the signals. A problem with this technique, however, is that the resulting sample rate of the signals might be insufficient to achieve a satisfactory signal-to-noise ratio (SNR). For example, assuming 16 channels, and that the sampler is configured to cycle through the channels at a frequency of 320 kHz, the sample rate for each signal would be only 20 kHz.

To address this challenge, embodiments of the present invention capitalize on the fact that, generally, the ECG signals acquired by those electrodes that are in contact with the tissue are more useful than the ECG signals from the other electrodes. In view of this fact, embodiments of the present invention allocate the sampling resources of the IC non-uniformly across the electrodes, giving preference to those electrodes that are in contact with the tissue, such that the SNR of the signals from these electrodes is increased.

For example, any signal from an electrode that is contact with the tissue may be passed through multiple channels simultaneously, such that this signal replaces one or more signals from other electrodes that are not in contact with the tissue. The sampler may thus, during at least one sampling cycle, sample the former signal multiple times, instead of sampling the latter signals, which in any case do not provide as much information as the former signal. Alternatively or additionally, the sampler may be configured to sample some channels more frequently than other channels, such that the more useful signals are sampled more frequently than the other signals.

System Description

Figure 1:
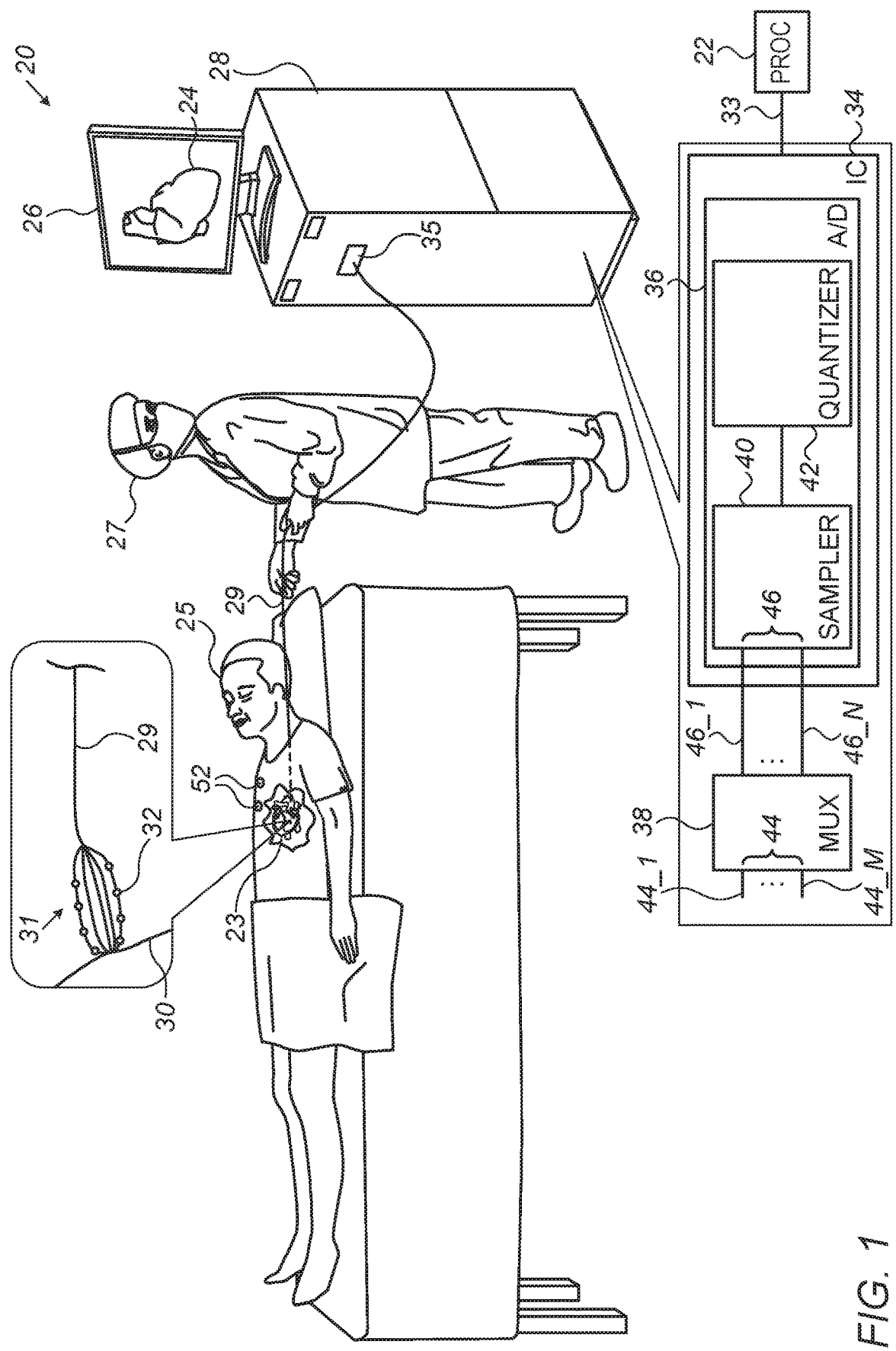
FIG. 1 is a schematic illustration of a system for acquiring intracardiac ECG signals, in accordance with some embodiments of the present invention.

Reference is initially made to FIG. 1, which is a schematic illustration of a system 20 for acquiring intracardiac ECG signals, in accordance with some embodiments of the present invention.

FIG. 1 depicts an electroanatomical mapping procedure, whereby a physician 27 navigates a catheter 29 within the heart 23 of a subject 25. Catheter 29 comprises a distal end 31, comprising a plurality of electrodes 32. By navigating catheter 29 within heart 23, physician 27 causes electrodes 32 to contact tissue 30 of the heart (e.g., myocardial tissue of the heart) at a plurality of different locations, such as to acquire intracardiac ECG signals from tissue 30. The ECG signals are received, and processed, by a processor (PROC) 22.

Catheter 29 further comprises one or more position sensors, which continually output tracking signals indicating the position and orientation of the catheter. Based on the tracking signals, processor 22 ascertains the respective positions of the electrodes, and hence, the respective anatomical location from which each ECG signal originates. Processor 22 further processes the ECG signals, such as to identify electrophysiological properties of the tissue. Based on this information, the processor constructs an electroanatomical map 24, in which a model of tissue 30 is annotated to show the electrophysiological properties of the tissue. Processor 22 may then display map 24 on a display 26.

In general, the processor may use any suitable technique to track the electrodes. For example, catheter 29 may comprise one or more electromagnetic position sensors, which, in the presence of an external magnetic field, generate signals that vary with the respective positions and orientations of the sensors. Based on these signals, the processor may ascertain the electrodes' respective locations. Alternatively, a plurality of external electrodes 52 coupled to subject 25 at various different locations may function as position sensors, in that processor 22 may ascertain the location of each electrode 32 based on the respective impedances between electrode 32 and external electrodes 52. As yet another alternative, the processor may use both electromagnetic tracking and impedance-based tracking, as described, for example, in U.S. Pat. No. 8,456,182, whose disclosure is incorporated herein by reference.

Typically, processor 22 resides within a computing console 28. Console 28 is coupled to catheter 29 via an electrical interface 35, such as a port or socket, such that the ECG signals from the electrodes, along with the various other signals described herein, are received by processor 22 via electrical interface 35.

Subsequently to being received by console 28, the ECG signals are digitized by system 20. For digitizing the ECG signals, system 20 comprises an analog-to-digital (A/D) converter 36, which is typically implemented on an integrated circuit (IC) 34, such as an ASIC. Converter 36 comprises a sampler 40, which receives the analog ECG signals over a set of channels 46. (FIG. 1 illustrates N channels 46, using the notation 46_1 . . . 46_N to indicate each of the individual channels.) Sampler 40 samples the ECG signals by sampling channels 46, i.e., by sampling the voltage or current carried over channels 46. Converter 36 further comprises a quantizer 42, which quantizes the samples received from sampler 40. Subsequently to digitizing a given ECG signal, converter 36 passes the signal to processor 22, which then processes the signal as described above.

(It is noted that the tracking signals, and/or the contact-monitoring signals described below, may also include analog signals that are digitized by converter 36 prior to being passed to processor 22.)

Typically, system 20 further comprises a multiplexer (MUX) 38, via which the A/D converter receives the ECG signals from electrodes 32. For example, a plurality of wires 44 may carry the ECG signals from electrodes 32, through the length of catheter 29, to multiplexer 38, and the multiplexer may pass the signals to the sampler over channels 46. Typically, each of wires 44 is distally connected to a different respective one of electrodes 32. (FIG. 1 illustrates M wires 44, using the notation 44_1 . . . 46_M to indicate each of the individual wires.) Typically, the number of wires is equal to the number of channels 46.

(It is noted that the different words "wire" and "channel" are used for ease of description only, and do not necessarily indicate any difference in construction or composition. In other words, the word "channel" may alternatively be used to describe each of wires 44, and the word "wire" may alternatively be used to describe each of channels 46.)

Processor 22 may be connected to IC 34 over any suitable wired or wireless communication interface 33. Processor 22 is configured to exchange communication with IC 34 over this communication interface, e.g., by receiving the digitized ECG signals from the IC, and/or by communicating instructions to sampler 40, as described below with reference to FIG. 3. Similarly, processor 22 may be connected to multiplexer 38 over any suitable wired or wireless communication interface (not shown in FIG. 1), and may exchange communication with the multiplexer over this interface, e.g., by communicating instructions to the multiplexer, as described below with reference to FIG. 2.

While the electrodes acquire the ECG signals from tissue 30, processor 22 receives, from one or more contact-indicating sensors, contact-indicating signals that indicate respective likelihoods of the electrodes being in contact with the tissue. In other words, the processor receives the contact-indicating signals and, based on these signals, computes the respective likelihoods of the electrodes being in contact with the tissue. In response to the likelihoods, the processor controls the sampling of the ECG signals, as further described below with reference to FIGS. 2-3. In particular, in response to the respective likelihoods for any two ECG signals being different from one another, the processor may cause the two ECG signals to be sampled, by sampler 40, at different respective sampling frequencies.

In general, any suitable contact-indicating sensors may be used for generating the contact-indicating signals. For example:

(i) One or more pressure sensors may be disposed at the distal end of catheter 29, as described, for example, in U.S. Pat. No. 6,915,149, whose disclosure is incorporated herein by reference. Responsively to the pressure measured by the pressure sensors, the processor may compute the likelihood of tissue contact for each of the electrodes.

(ii) Alternatively or additionally, the aforementioned position sensors (e.g., external electrodes 52) may function as contact-indicating sensors, and the aforementioned tracking signals may function as contact-indicating signals, in that the processor may compute the likelihoods of tissue contact from the respective positions of the electrodes ascertained from the tracking signals. For example, the processor may fit a model of distal end 31 to the electrode positions, and then compute the likelihood of tissue contact responsively to the configuration of the model, as described, for example, in U.S. patent application Ser. No. 15/610,865, filed Jun. 1, 2017, whose disclosure is incorporated herein by reference.

(iii) Alternatively or additionally, external electrodes 52, even if not used for tracking the electrodes' positions, may be used as contact-indicating sensors, in that the processor may receive, from external electrodes 52, signals that indicate changes in impedance between electrodes 32 and external electrodes 52, and then compute the likelihood of tissue contact responsively to these changes in impedance. (In general, the impedance of tissue is greater than the impedance of blood, such that, as any given electrode approaches the tissue, the impedance between the given electrode and the external electrodes increases.) To this end, the processor may use a baseline impedance map, as described, for example, in U.S. patent application Ser. No. 15/788,286, filed Oct. 19, 2017, whose disclosure is incorporated herein by reference.

It is noted that, in the context of the present application, including the claims, an electrode may be said to "contact" the tissue, as long as the electrode is within a given threshold distance of the tissue. This threshold may be defined, implicitly, by whichever method is used to ascertain tissue contact. For example, if impedance measurements are used to ascertain tissue contact, the electrode may be said to contact the tissue if the measured impedance exceeds a baseline impedance by more than a particular threshold.

In general, processor 22 may be embodied as a single processor, or a cooperatively networked or clustered set of processors. Processor 22 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Notwithstanding the particular scenario depicted in FIG. 1, it is noted that the sampling techniques described herein may be applied to any procedure in which intracardiac ECG signals, or any other type of intrabody signals, are acquired. For example, the sampling techniques described herein may be applied to the acquisition of intracardiac ECG signals during an electroanatomical mapping performed as part of a cardiac ablation procedure.

Sampling the ECG Signals

Figure 2:
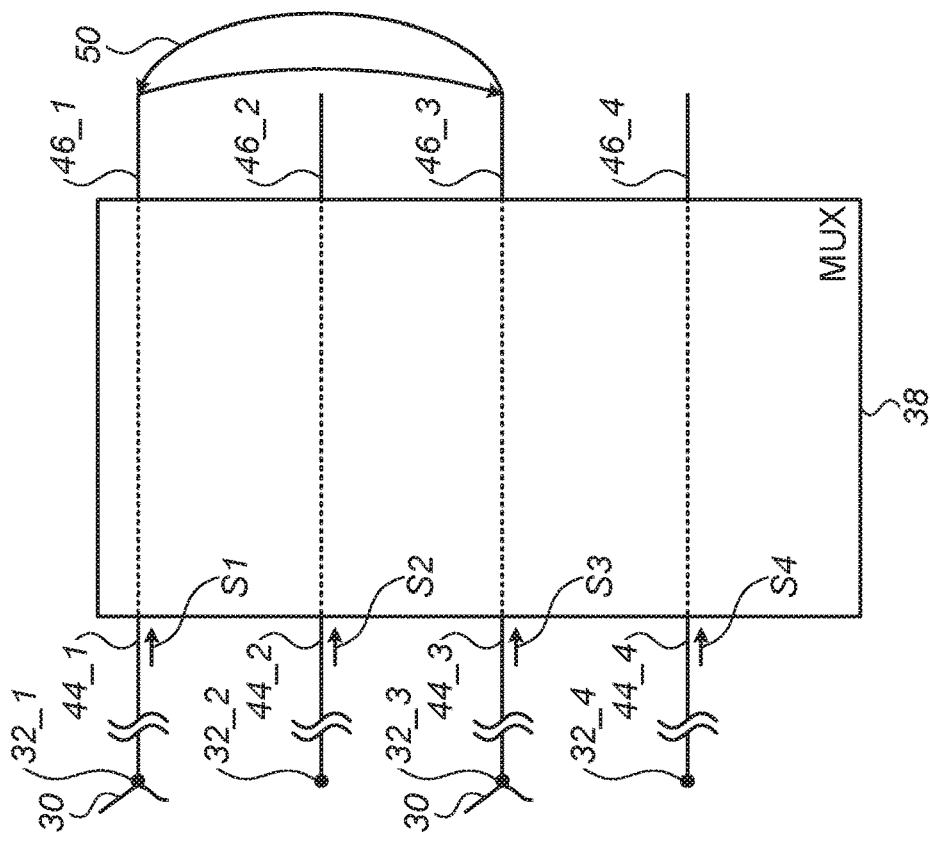
FIGS. 2-3 are schematic illustrations of sampling techniques, in accordance with some embodiments of the present invention.
Figure 3:
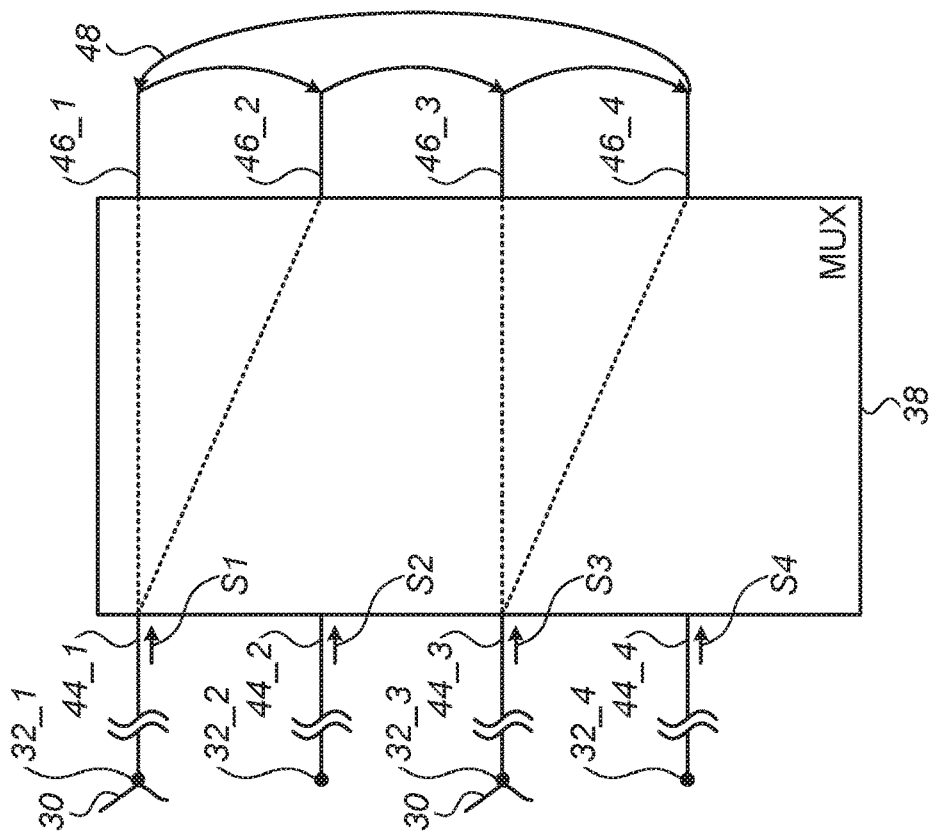

Reference is now made to FIGS. 2-3, which are schematic illustrations of sampling techniques, in accordance with some embodiments of the present invention.

As described above with reference to FIG. 1, multiplexer 38 receives a respective ECG signal from each of the electrodes, over a respective wire 44. Each of FIGS. 2-3 thus shows a first signal S1 from a first electrode 32_1 received over a first wire 44_1, a second signal S2 from a second electrode 32_2 received over a second wire 44_2, a third signal S3 from a third electrode 32_3 received over a third wire 44_3, and a fourth signal S4 from a fourth electrode 32_4 received over a fourth wire 44_4. The received signals are passed, by multiplexer 38, over channels 46, and sampler 40 samples the signals by repeatedly iterating over (or "cycling through") some or all of the channels. For example, as depicted in FIG. 2 by a set of arrows 48, the sampler may repeatedly sample, in sequence, a first channel 46_1, a second channel 46_2, a third channel 46_3, and a fourth channel 46_4.

Each of FIGS. 2-3 depicts a scenario in which, at a given moment in time, first electrode 32_1 and third electrode 32_3 are in contact with tissue 30, whereas second electrode 32_2 and fourth electrode 32_4 are not in contact with the tissue. In this scenario, processor 22, by processing the relevant contact-indicating signals as described above with reference to FIG. 1, computes a greater likelihood of tissue contact for first electrode 32_1 and third electrode 32_3. Responsively thereto, processor 22 causes each of first signal S1 and third signal S3 to be sampled at a greater frequency than the frequency at which second signal S2 and fourth signal S4 are sampled, as further described below.

In some embodiments, responsively to the contact-indicating signals, the processor computes a tissue-contact likelihood of 1 or 0 for each of the electrodes, i.e., the processor renders, for each of the electrodes, a "yes" or "no" decision that indicates whether contact with the tissue has been ascertained. For example, assuming the aforementioned impedance-based technique for generating tissue-contact signals, the processor may ascertain tissue contact for a particular electrode in response to the impedance between the electrode and at least one of external electrodes 52 deviating from a baseline impedance by more than a predefined threshold. Alternatively, the processor may allow the likelihoods to attain any suitable number of intermediate values between 0 and 1, or between any other suitable limits, such that each likelihood is effectively a level of confidence with which tissue contact is ascertained. For example, assuming the impedance-based technique, the processor may compute the level of confidence as an increasing function of the deviation of the measured impedance from the baseline impedance.

For example, for the scenario depicted in FIGS. 2-3, the processor may ascertain that each of the first and third electrodes contacts the tissue, whereas each of the other electrodes does not contact the tissue. Responsively thereto, the processor may cause each of first signal S1 and third signal S3 to be sampled at a first sampling frequency, and each of the other signals to be sampled at a second, lower sampling frequency. Alternatively, in response to ascertaining the contact of first electrode 32_1 with a level of confidence that is greater than the level of confidence for third electrode 32_3, the processor may cause first signal S1 to be sampled at a first sampling frequency, third signal S3 to be sampled at a second, lower frequency, and the other two signals to be sampled at a third, lowest frequency.

In some embodiments, as illustrated in FIG. 2, the processor causes two or more ECG signals to be sampled at different respective sampling frequencies by causing multiplexer to pass the ECG signals to sampler 40 over different respective numbers of the channels. Thus, for example, processor 22 may cause multiplexer 38 to pass each of the first and third signals to the sampler over a number of channels that is greater (or over respective numbers of channels that are both greater) than the number of channels over which each of the second and fourth signals are passed to the sampler. As a result of the first and third signals being carried over a greater number of channels, the sampler, as it cycles through the channels, samples the first and third signals at a greater frequency. (Processor 22 notifies converter 36 of any changes to the configuration of the multiplexer, i.e., any changes to the connections between wires 44 and channels 46, such that the converter knows the signal to which any given sample belongs.)

For example, the processor may instruct the multiplexer to pass the first and third signals to the sampler without passing the second and fourth signals to the sampler, during at least one sampling cycle of the sampler, thus causing the second and fourth signals to not be sampled during the sampling cycle. For example, assuming that the default configuration of the multiplexer is to connect each channel to its corresponding wire (such that, for each i=1 . . . 4, channel 46_i is connected to wire 44_i, as shown in FIG. 3), the processor may instruct the multiplexer to connect second channel 46_2 to first wire 44_1 instead of to second wire 44_2, and to connect fourth channel 46_4 to third wire 44_3 instead of to fourth wire 44_4. Thus, during at least one cycle of the sampler, each of the first and third cycles may be sampled twice, while the second and fourth channels may not be sampled at all. Alternatively, assuming that, as described above by way of example, the likelihood of tissue contact is greater for the first electrode than for the third electrode, the processor may, for example, instruct the multiplexer to connect the first wire to each of the first, second, and fourth channels, such that the first signal is carried over three of the channels, and the third signal is carried over one of the channels.

Typically, it is advantageous to acquire at least some samples of every signal, including the "non-tissue-contact signals" acquired by electrodes that are not in contact with the tissue. Hence, the processor may vary the respective numbers of channels over which the signals are carried over multiple sampling cycles of the sampler (even without any changes to the tissue-contact status of the electrodes), such that the sampling frequency of the "tissue-contact signals" is greater than that of the non-tissue-contact signals, yet at least some samples of the non-tissue-contact signals are acquired. Alternatively or additionally, the processor may vary the respective numbers of channels over which the signals are carried, such that each of the tissue-contact signals is sampled at a frequency corresponding to the confidence level with which tissue contact is ascertained.

For example, the processor may repeatedly alternate the configuration of multiplexer 38 shown in FIG. 2 with the default configuration of the multiplexer, such that, during every two consecutive sampling cycles, three samples of each of signals S1 and S3 are acquired, and one sample of each of signals S2 and S4 is acquired. As another example, responsively to a greater confidence level for first electrode 32_1 than for third electrode 32_3, the processor may repeatedly alternate the configuration shown in FIG. 2 with a configuration in which first signal S1 is carried over three channels, and third signal S3 over one channel (as described above), such that first signal S1 is sampled with a frequency of 2.5 samples/cycle, and third signal S3 is sampled at 1.5 samples/cycle.

Alternatively or additionally to changing the connections between wires 44 and channels 46, the processor may change the sampling routine of sampler 40, as illustrated in FIG. 3. In particular, the processor may cause the sampler to sample some channels more frequently than other channels, rather than simply iterating sequentially over the channels. For example, as shown in FIG. 3, the processor may maintain the default configuration of the multiplexer, such that the multiplexer passes the ECG signals to the sampler over respective ones of the channels, but cause the sampler to sample the channels at different respective sampling frequencies. For example, in response to ascertaining that the first and third electrodes are in contact with tissue 30, the processor may, as indicated by a pair of arrows 50, instruct the sampler to alternate between the first and third channels during at least one sampling cycle of the sampler, such that, during the sampling cycle, two samples are obtained from each of the first and third signals, without obtaining any samples from the second and fourth signals.

Analogously to that which was described above with reference to FIG. 2, the processor may set the sampling routine of sampler 40 responsively to the confidence levels with which tissue contact is ascertained. Alternatively or additionally, the processor may vary the sampling routine of sampler 40 over multiple sampling cycles of the sampler (even without any changes to the tissue-contact status of the electrodes), such as to give each signal a desired sampling frequency.

(It is noted that, in embodiments in which processor 22 controls the sampler responsively to ascertaining the tissue-contact status of the electrodes, system 20 does not necessarily comprise multiplexer 38; rather, the ECG signals may be carried directly to the sampler over wires 44.)

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system, comprising:
   sample-and-hold circuitry, configured to sample a plurality of intracardiac electrocardiographic (ECG) signals acquired by respective electrodes disposed within a heart of a subject;
   a processor, configured to:

receive, from one or more contact-indicating sensors, contact-indicating signals that indicate respective likelihoods of the electrodes being in contact with tissue of the heart, and in response to the likelihoods being different from each other, cause the ECG signals to be sampled, by the sample-and-hold circuitry, at different respective sampling frequencies; and a multiplexer, configured to:
receive the ECG signals from the electrodes, and
pass the received ECG signals, over a set of channels, to the sample-and-hold circuitry,
wherein the sample-and-hold circuitry is configured to sample the ECG signals by sampling the channels.

2. The system according to claim 1, wherein the processor is configured to cause the ECG signals to be sampled at the different respective sampling frequencies by causing the multiplexer to pass the ECG signals to the sample-and-hold circuitry over different respective numbers of the channels.

3. The system according to claim 2, wherein the processor is configured to cause the ECG signals to be sampled at the different respective sampling frequencies by varying the respective numbers of the channels over multiple sampling cycles of the sample-and-hold circuitry.

4. The system according to claim 1, wherein the multiplexer is configured to pass the ECG signals to the sample-and-hold circuitry over respective ones of the channels, and wherein the processor is configured to cause the ECG signals to be sampled at the different respective sampling frequencies by causing the sample-and-hold circuitry to sample the respective ones of the channels at the different respective sampling frequencies.

5. The system according to claim 1,
wherein the electrodes include a first electrode and a second electrode,
wherein the ECG signals include a first ECG signal from the first electrode, and a second ECG signal from the second electrode,
wherein the likelihoods include a first likelihood of the first electrode being in contact with the tissue, and a second likelihood of the second electrode being in contact with the tissue, and
wherein the processor is configured to cause the first ECG signal to be sampled at a greater frequency than the second ECG signal, in response to the first likelihood being greater than the second likelihood.

6. The system according to claim 5, wherein the processor is configured to cause the second ECG signal to not be sampled during at least one sampling cycle of the sample-and-hold circuitry, in response to the first likelihood being greater than the second likelihood.

7. A method, comprising:
receiving, from one or more contact-indicating sensors, contact-indicating signals that indicate respective likelihoods of a plurality of electrodes being in contact with tissue of a heart of a subject, while the electrodes acquire respective intracardiac electrocardiographic (ECG) signals from the tissue; and
in response to the likelihoods being different from each other, causing the ECG signals to be sampled, by sample-and-hold circuitry, at different respective sampling frequencies, wherein a multiplexer receives the ECG signals from the electrodes and passes the received ECG signals, over a set of channels, to the sample-and-hold circuitry, and
wherein the sample-and-hold circuitry samples the ECG signals by sampling the channels.

8. The method according to claim 7, wherein causing the ECG signals to be sampled at the different respective sampling frequencies comprises causing the ECG signals to be sampled at the different respective sampling frequencies by causing the multiplexer to pass the ECG signals to the sample-and-hold circuitry over different respective numbers of the channels.

9. The method according to claim 8, wherein causing the ECG signals to be sampled at the different respective sampling frequencies comprises causing the ECG signals to be sampled at the different respective sampling frequencies by varying the respective numbers of the channels over multiple sampling cycles of the sample-and-hold circuitry.

10. The method according to claim 7,
wherein the multiplexer passes the ECG signals to the sample-and-hold circuitry over respective ones of the channels, and
wherein causing the ECG signals to be sampled at the different respective sampling frequencies comprises causing the ECG signals to be sampled at the different respective sampling frequencies by causing the sample-and-hold circuitry to sample the respective ones of the channels at the different respective sampling frequencies.

11. The method according to claim 7,
wherein the electrodes include a first electrode and a second electrode,
wherein the ECG signals include a first ECG signal from the first electrode, and a second ECG signal from the second electrode,
wherein the likelihoods include a first likelihood of the first electrode being in contact with the tissue, and a second likelihood of the second electrode being in contact with the tissue, and
wherein causing the ECG signals to be sampled at the different respective sampling frequencies comprises, in response to the first likelihood being greater than the second likelihood, causing the first ECG signal to be sampled at a greater frequency than the second ECG signal.

12. The method according to claim 11, wherein causing the first ECG signal to be sampled at the greater frequency comprises causing the first ECG signal to be sampled at the greater frequency by causing the second ECG signal to not be sampled during at least one sampling cycle of the sample-and-hold circuitry.

13. A computer software product comprising a tangible non-transitory computer-readable medium in which program instructions are stored, which instructions, when read by a processor, cause the processor to:
receive, from one or more contact-indicating sensors, contact-indicating signals that indicate respective likelihoods of a plurality of electrodes being in contact with tissue of a heart of a subject, while the electrodes acquire respective intracardiac electrocardiographic (ECG) signals from the tissue, and
in response to the likelihoods being different from each other, cause the ECG signals to be sampled, by sample-and-hold circuitry, at different respective sampling frequencies, wherein a multiplexer receives the ECG signals from the electrodes and passes the received ECG signals, over a set of channels, to the sample-and-hold circuitry,
wherein the sample-and-hold circuitry is configured to sample the ECG signals by sampling the channels, and
wherein the instructions cause the processor to cause the ECG signals to be sampled at the different respective sampling frequencies by causing the multiplexer to pass the ECG signals to the sample-and-hold circuitry over different respective numbers of the channels.

14. The computer software product according to claim 13, wherein the instructions cause the processor to cause the ECG signals to be sampled at the different respective sampling frequencies by varying the respective numbers of the channels over multiple sampling cycles of the sample-and-hold circuitry.

15. The computer software product according to claim 13,
wherein the electrodes include a first electrode and a second electrode,
wherein the ECG signals include a first ECG signal from the first electrode, and a second ECG signal from the second electrode,
wherein the likelihoods include a first likelihood of the first electrode being in contact with the tissue, and a second likelihood of the second electrode being in contact with the tissue, and
wherein the instructions cause the processor to cause the first ECG signal to be sampled at a greater frequency than the second ECG signal, in response to the first likelihood being greater than the second likelihood.

16. The computer software product according to claim 15, wherein the instructions cause the processor to cause the second ECG signal to not be sampled during at least one sampling cycle of the sample-and-hold circuitry, in response to the first likelihood being greater than the second likelihood.

17. A computer software product comprising a tangible non-transitory computer-readable medium in which program instructions are stored, which instructions, when read by a processor, cause the processor to:
receive, from one or more contact-indicating sensors, contact-indicating signals that indicate respective likelihoods of a plurality of electrodes being in contact with tissue of a heart of a subject, while the electrodes acquire respective intracardiac electrocardiographic (ECG) signals from the tissue, and
in response to the likelihoods being different from each other, cause the ECG signals to be sampled, by sample-and-hold circuitry, at different respective sampling frequencies, wherein a multiplexer receives the ECG signals from the electrodes and passes the received ECG signals, over different respective channels, to the sample-and-hold circuitry,
wherein the sample-and-hold circuitry is configured to sample the ECG signals by sampling the channels, and
wherein the instructions cause the processor to cause the ECG signals to be sampled at the different respective sampling frequencies by causing the sample-and-hold circuitry to sample the respective channels at the different respective sampling frequencies.

* * * * *